United States Patent [19]

Kaspari et al.

[11] Patent Number: 5,533,511
[45] Date of Patent: Jul. 9, 1996

[54] APPARATUS AND METHOD FOR NONINVASIVE BLOOD PRESSURE MEASUREMENT

[75] Inventors: William J. Kaspari, Portola Valley; Roger A. Stern, Cupertino, both of Calif.

[73] Assignee: Vital Insite, Incorporated, Portola Valley, Calif.

[21] Appl. No.: 177,448

[22] Filed: Jan. 5, 1994

[51] Int. Cl.$^6$ ...................................................... A61B 5/00
[52] U.S. Cl. ...................... 128/672; 128/681; 128/687; 128/630; 128/748; 128/668; 128/696
[58] Field of Search .............................. 128/632, 633–5, 128/637, 661.08, 661.09, 662.1, 664–668, 672–696, 702, 703–705, 713, 716–732, 736, 748

[56] References Cited

U.S. PATENT DOCUMENTS

| | | |
|---|---|---|
| 4,269,193 | 5/1981 | Eckerle . |
| 4,406,289 | 9/1983 | Wesseling et al. . |
| 4,423,738 | 1/1984 | Newgard . |
| 4,475,554 | 10/1984 | Hyndman . |
| 4,510,940 | 4/1985 | Wesseling . |
| 4,524,777 | 6/1985 | Kissioka et al. . |
| 4,539,997 | 9/1985 | Wesseling et al. . |
| 4,669,485 | 6/1987 | Russell . |
| 4,718,426 | 1/1988 | Russell . |
| 4,718,427 | 1/1988 | Russell . |
| 4,718,428 | 1/1988 | Russell . |
| 4,799,491 | 1/1989 | Eckerle . |
| 4,802,488 | 2/1989 | Eckerle . |
| 4,846,189 | 7/1989 | Sun . |
| 4,869,261 | 9/1989 | Penaz . |
| 4,960,128 | 10/1990 | Gordon et al. . |
| 5,033,471 | 7/1991 | Yokoe et al. . |
| 5,099,853 | 3/1992 | Uemura et al. ...................... 128/681 |
| 5,165,416 | 11/1992 | Shinoda et al. . |
| 5,339,818 | 8/1994 | Baker et al. ...................... 128/677 |
| 5,390,679 | 2/1995 | Martin ................................ 128/713 |

FOREIGN PATENT DOCUMENTS

| | | |
|---|---|---|
| 0048060 | 3/1982 | European Pat. Off. . |
| 0443267A1 | 2/1990 | European Pat. Off. . |

*Primary Examiner*—Angela D. Sykes
*Assistant Examiner*—Robert L. Nasser, Jr.
*Attorney, Agent, or Firm*—Flehr, Hohbch, Test, Albritton & Herbert

[57] ABSTRACT

A blood pressure monitor for determining a patient's blood pressure comprises a processor attached to a first input device for receiving an initial input representing the patient's absolute blood pressure, and a noninvasive sensor attached to the patient for measuring at least one physiological function. The processor executes a procedure for evaluating the initial input and the sensed physiological function to determine the patient's blood pressure. A method for determining a patient's blood pressure comprises the steps of storing an initial input representing a patient's absolute blood pressure, noninvasively sensing at least one of the patient's physiological functions, and evaluating the initial input and the sensed input to determine the patient's blood pressure. The present invention can also be used to analyze and track other physiological variables such as vascular wall compliance, changes in the strength of ventricular contractions, changes in vascular resistance, changes in fluid volume, changes in cardiac output, myocardial contractility and other related factors.

30 Claims, 9 Drawing Sheets

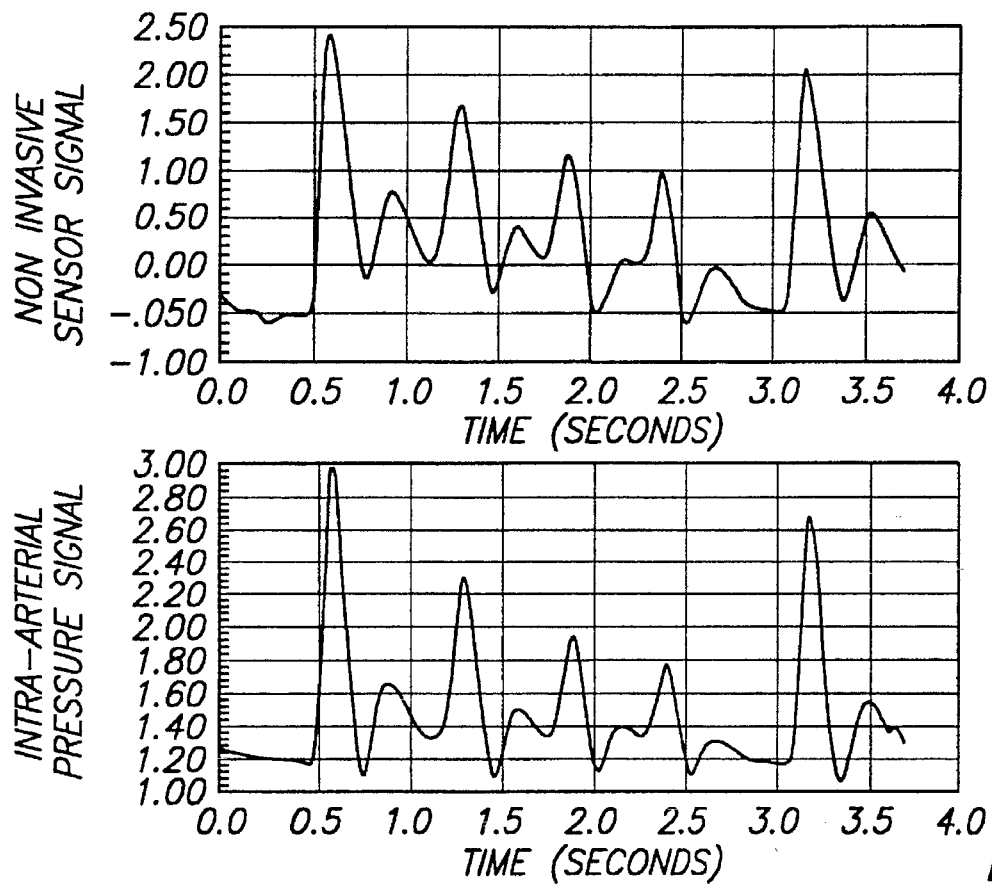
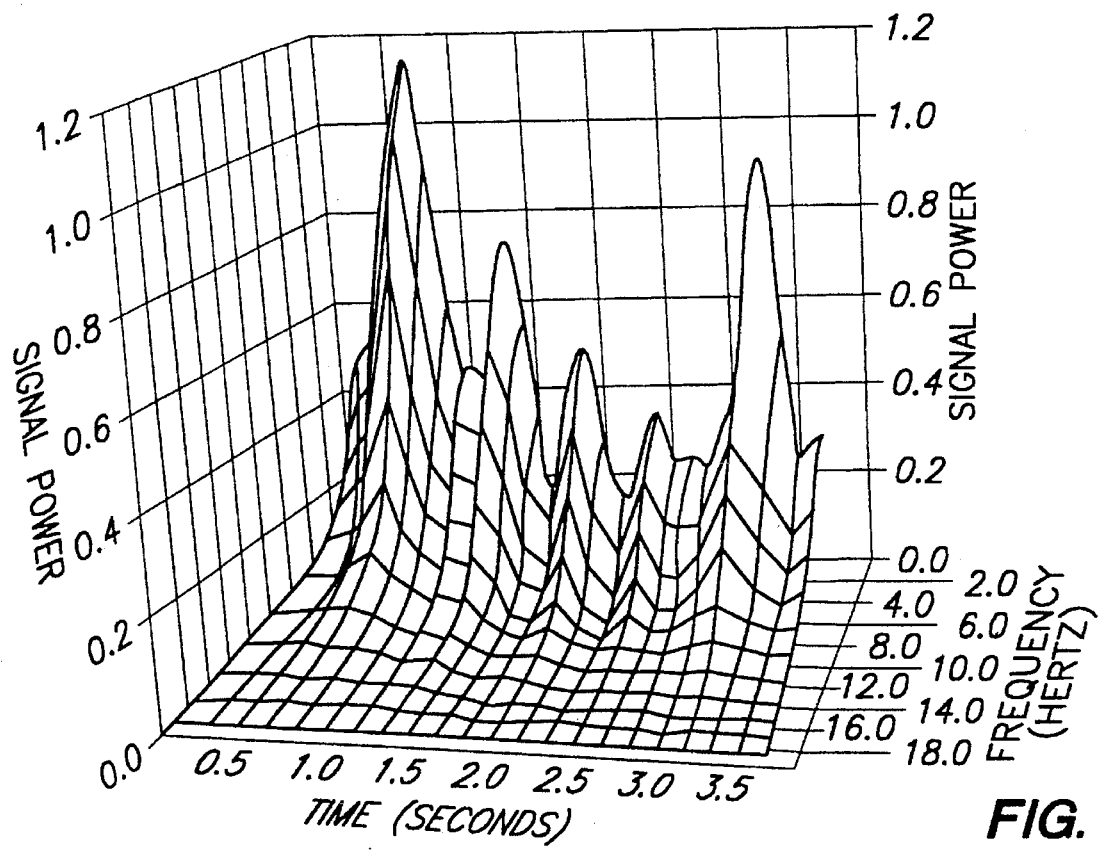
FIG. 5
FIG. 6

APPARATUS AND METHOD FOR NONINVASIVE BLOOD PRESSURE MEASUREMENT

FIELD OF THE INVENTION

The present invention relates generally to an apparatus and method for analyzing the waveshape of an electrical waveform using pattern recognition techniques. More particularly, it relates to an apparatus and method of using these techniques to analyze a signal obtained from a noninvasive arterial sensor to provide a continuous (beat-to-beat) measure of an individual's blood pressure and other clinically important parameters.

BACKGROUND OF THE INVENTION

Blood pressure is the force within the arterial system of an individual that ensures the flow of blood and delivery of oxygen and nutrients to the tissue. Prolonged reduction or loss of pressure severely limits the amount of tissue perfusion and could therefore result in damage to or even death of the tissue. Although some tissues can tolerate hypoperfusion for fairly long periods of time, the brain, heart and kidneys are very sensitive to a reduction in blood flow. Thus, during surgery, blood pressure is a frequently monitored vital sign. During and after surgery, blood pressure is affected by the type of surgery and physiological factors such as the body's response to the surgery. Moreover, during and after surgery, blood pressure is manipulated and controlled using various medications. Often, these physiological factors and the given medications result in a situation requiring immediate blood pressure measurement, and corrective action.

The most commonly used method of controlling an individual's blood pressure, particularly during surgery and in the critical period following surgery, is with vasoactive medications. These agents control the individual's blood pressure primarily by altering the resistance to blood flow in the peripheral arteries. For example, a vasodilating agent reduces peripheral resistance by increasing arterial compliance, and thereby reduces blood pressure. Conversely, a vasoconstrictor increases peripheral resistance by decreasing arterial compliance, and thereby increases blood pressure. Alternatively, inotropic agents can adjust the strength of the heart's contractions to modify blood pressure.

In some clinical situations, dramatic changes in blood pressure can occur instantaneously. For example, a sudden change in pressure may occur due to a reaction to drug therapy. Also, patient reactions to the surgery, sudden occlusion of an artery due to an embolism, or even sudden cardiac arrest are a few of the possibilities. It is very important to detect these sudden changes immediately, and to insure that the direction and amount of the changes be accurate within certain limits. Conversely, it is equally important that false indications of significant blood pressure changes do not occur.

Because of the patient's changes in blood pressure, it is important to constantly monitor blood pressure. The traditional method of measuring blood pressure is with the use of a stethoscope, occlusive cuff and pressure manometer. However, this technique is slow, subjective in nature, requires the intervention of a skilled clinician and does not provide the timely readings frequently required in critical situations.

For these reasons, two methods of measuring blood pressure have been developed: noninvasive, intermittent methods that use an automated occlusive cuff device; and invasive, continuous (beat-to-beat) measurements.

The noninvasive cuff method does not have the inherent disadvantages of the invasive technique including the risk of embolization, nerve damage, infection, bleeding and vessel wall damage. It also does not provide the continuous beat-to-beat pressure variations obtainable with the invasive method. Further, the noninvasive cuff method typically requires 15 to 45 seconds to obtain a measurement, and since it is an occlusive technique, the method should allow a minimum of 15 seconds to ensure sufficient venous recovery. Thus, at best there is typically ½ to 1 minute between updated pressure measurements. When fast acting medications are administered, this is an inordinately long amount of time to wait for an updated pressure reading. Also, frequent cuff inflations over extended periods of time may result in ecchymosis and/or nerve damage in the area underlying the cuff.

Several systems have been developed to address the need for continuous, noninvasive blood pressure measurement. These systems are described below.

The following patents show a technique known as photoplethysmography. Wesseling et al., European Patent Document 0048060 (1982), and U.S. Pat. Nos. 4,406,289 (1983), 4,510,940 and 4,539,997 (1985); Hyndman, U.S. Pat. No. 4,475,554 (1984); Kisioka, U.S. Pat. No. 4,524,777 (1985); Sun, U.S. Pat. No. 4,846,189 (1989); and Penaz, U.S. Pat. No. 4,869,261 (1989), all relate to this technique. They are commercially implemented in a device known as the Finapres.

The Finapres uses a small inflatable air cuff containing an infrared photoplethysmograph. The cuff is applied to one of the subject's fingers or thumb, and the plethysmograph measures the absorption at a wavelength specific for hemoglobin. The device first measures the individual's mean arterial pressure, and then varies the cuff pressure around the finger to maintain the transmural pressure at zero as determined by the plethysmograph. The device tracks the intra-arterial pressure wave by adjusting the cuff pressure to maintain the optical absorption constant at all times.

There are three major disadvantages to this technique. First, when there exists peripheral vasoconstriction, poor vascular circulation, or other factors, the blood pressure measured in a finger is not necessarily representative of central blood pressure. Second, the signal amplitude detected by the photoplethysmograph is a function of the changes in the diameter of the artery within the finger, and is determined by the compliance characteristics of the artery. The device maintains this amplitude at a constant value. This value, or set point, must correspond to the point of zero transmural stress in order to determine the correct pressure. During surgery for example, the device cannot differentiate between changes in photoplethysmograph amplitude due to intra-arterial pressure changes and those due to arterial wall compliance changes. Consequently, the Finapres cannot accurately respond to pressure changes caused by changes in vasomotor tone. Third, maintaining continuous cuff pressure causes restriction of the circulation in the finger being used, which is uncomfortable when maintained for extended periods of time such as during surgery or during a stay in an acute care unit.

Russel, U.S. Pat. Nos. 4,669,485 (1987), 4,718,426, 4,718,427 and 4,718,428 (1988), show a device using a conventional blood pressure cuff applied to a person's upper arm to sense an oscillometric signal. The subject's blood pressure is obtained initially by the oscillometric technique, and then changes in the oscillometric signal indicate changes from this initial reference pressure.

There are two major drawbacks to this technique. First, the use of a large air bag as the sensing device provides a means for detecting the fundamental and lower harmonics of the blood pressure signal (up to a few Hertz), but also acts to attenuate many higher order harmonics containing key information relating to blood pressure variations. Second, the use of a cuff to detect the oscillometric signal creates a signal that is very sensitive to patient movement. Since patient movement is often encountered during surgery or in critical care situations, the device requires frequent recalibration to be accurate.

Eckerle, U.S. Pat. Nos. 4,269,193 (1981), 4,799,491 and 4,802,488 (1989); Newgard, U.S. Pat. No. 4,423,738 (1984); Yokoe et al., U.S. Pat. No. 5,033,471 (1991); and Shinoda et al., U.S. Pat. No. 5,165,416 (1992), describe sensing means for detecting the pressure wave in the underlying artery of an individual using a technique known as the tonometric technique.

A commercial implementation of this technique is a device manufactured by Nippon Colin. This device uses a multi-element piezoresistive sensor to noninvasively detect the blood pressure wave at the radial artery. This signal is then processed and changes in its amplitude are used to interpret changes to the pressure values obtained using the conventional oscillometric technique.

The major drawback to this technique lies in the method of interpreting changes to the waveform signal. Reliance solely on amplitude changes is misleading since the signal amplitude may increase or decrease with an increase in blood pressure, etc. Secondly, it is dependent on the artery being exactly flat, and variations in artery flatness can introduce errors. It also assumes that the selected sensing element is small with respect to the artery, and that it does not move from its position centered over the artery. Thus, any movement such as that often encountered in surgery or critical care situations will reduce the accuracy of this device.

Smith, European Patent Document 0 443 267 A1 (1991), describes a technique using changes in pulse transit time to provide a continuous, noninvasive measure of blood pressure. This technique was developed by Sentinel Monitoring, Inc., of Indianapolis, Ind., and uses a duplicity of photometric sensors similar to those used with oximeters. Typically, one sensor is applied to the subject's ear lobe, and the other to a finger. The sensors are used for determining changes in the arrival time of the pulse at each of these sites, and to determine changes in local blood volume. Following an initial calibration pressure measurement obtained with a conventional blood pressure cuff, the Smith device adjusts these pressures by interpreting changes in the pulse transit time and in the optical density of the photoplethysmograph signal.

There are two disadvantages to the Smith technique. First, changes in pulse transit time are very small along major arteries. As a result, small errors caused by patient movement or noise render questionable data. Second, small variations in photoplethysmographic waveform morphology or sensor noise can generate measurement errors greater than the sensitivity of the technique to changes in blood pressure.

Gordon, et al., U.S. Pat. No. 4,960,128 basically shows a method of determining blood pressure by measuring a single harmonic of the frequencies and displacements of the patient's arterial wall. In Gordon, initial (absolute) blood pressure values are obtained with a cuff and stethoscope or via an intermittent automated cuff machine, and manually entered into the device as initial reference values. A continuous sensor signal is supplied by a noninvasive sensor attached to the patient's skin above an artery. The sensor signal is filtered, amplified and then sampled. This time sampled sensor data is then Fourier transformed into the frequency domain and normalized at 1024 point intervals.

As blood pressure changes, the reported frequencies and their relative amplitudes change. A comparison is made between the fundamental frequency of the present signal and the initial signal. For each shift in frequency (+ or −) of 1 Hz, the offset is adjusted correspondingly to yield a change of 5 mm Hg. Thus, Gordon shows a device in which the patient's blood pressure is determined based on the difference in position of the fundamental frequency of the sensor signal and initial signal.

The technique described in the Gordon reference does not adequately account for the plurality of factors that can reflect a change in blood pressure. There is a multitude of waveshapes that can accompany a given set of blood pressure values, and the Gordon technique is limited by its function of comparing the frequency with the maximum amplitude of the current signal to that of the initial signal to determine blood pressure.

SUMMARY OF THE INVENTION

The present invention has the following benefits and capabilities. It can measure and interpret a signal related to the actual blood pressure in the artery. It can evaluate both the amplitude and phase relationships of many relevant frequency components of the blood pressure waveform. It can analyze the blood pressure waveform in both the frequency domain and the time domain. It can use sophisticated pattern recognition techniques to analyze complex changes in the blood pressure waveform.

These features are novel because they teach the utilization of information present in the shape of the blood pressure waveform to determine ongoing changes in blood pressure and other clinically significant physiological parameters.

A basic concept underlying the need for the present invention is that a patient's blood pressure waveform changes regardless of whether the blood pressure change is a result of exogenous drug therapy or endogenous effects. The term "waveform change" here is meant to include a change in the magnitude and/or phase of the Fourier components that compose the waveform, as well as the time varying amplitude changes.

A preferred embodiment of a blood pressure monitor for determining a patient's blood pressure comprises a processor attached to a first input device for receiving an initial input signal representing the patient's absolute blood pressure, and a noninvasive sensor attached to the patient for measuring at least one physiological function including heart beat, arterial displacement frequency, arterial displacement magnitude, and arterial pressure, and creating a sensor input signal responsive to the measured physiological function. The processor has the capability to perform analog to digital conversion on these signals and to perform digital signal processing procedures on the sampled data. The processor also has the capability to perform at least one procedure for evaluating the initial input and the noninvasive sensor input to determine the patient's current blood pressure.

A method for determining a patient's blood pressure comprises the steps of storing an initial input representing a patient's absolute blood pressure, noninvasively sensing at least one of the patient's physiological functions, and evaluating the initial input and the sensed input to determine the patient's current blood pressure.

In the preferred embodiment, a neural network is trained to correlate the changes in the time and/or frequency characteristics of the waveform with changes in blood pressure. The neural network creates a set of predetermined features that are stored in a processor memory accessible to the processor. The processor compares current noninvasive sensor waveform features with the predetermined features to determine the patient's blood pressure.

It is a further function of this device to provide a means for automatically initiating a calibration reading and to otherwise alert the user any time a significant short term change in blood pressure is determined.

Various noninvasive sensors have been developed for sensing waveforms such as blood pressure waveforms. These sensor types include piezoelectric, piezoresistive, impedance plethysmography, photoplethysmography, various types of strain gauges, air cuffs, and other devices. It is the intent here to describe a method and apparatus that can use any sensor that provides a waveform related to blood pressure.

BRIEF DESCRIPTION OF THE DRAWINGS

FIG. 5 shows two blood pressure waveforms recorded simultaneously in a fourth patient also undergoing surgery. The 5A waveform was obtained with a noninvasive piezoelectric sensor. The 5B waveform was obtained with an intra-arterial catheter.

FIG. 6 is a graphical representation of the noninvasive waveform of FIG. 5A. This graph shows both the time and frequency components of the waveform, and depicts the changing energy content, and the changing features that occur over time from one beat to the next.

DETAILED DESCRIPTION OF A PREFERRED EMBODIMENT

To clarify the theory of the present invention, information relating to the significance of wave shapes will be presented. Blood pressure waveforms are used as examples.

The waveforms referred to in the following discussions were obtained with a noninvasive sensor using a piezoelectric film as outlined in O'Sullivan, et al., U.S. patent application Ser. No. 08/059,425. This sensor provides a continuous waveform when the sensor is placed on skin over an individual's artery. The detected waveform is responsive to the actual blood pressure wave within the underlying artery.

Figure 1:
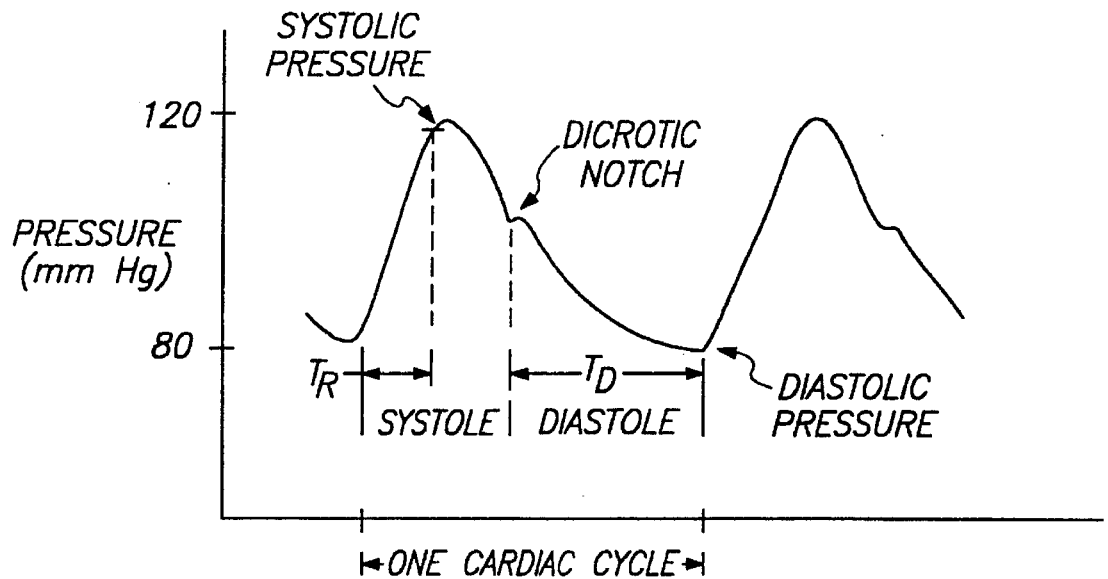
FIG. 1 shows the shape and a few of the defining characteristics of a typical blood pressure waveform.

FIG. 1 shows a typical blood pressure waveform. This waveform is characterized by a rapid increase in pressure from the time immediately following the onset of the contraction of the left ventricle, to a peak value corresponding to the peak (systolic) pressure. Blood forced from the left ventricle into the aorta, and from there into the smaller vessels, creates a pressure wave. Following completion of the ventricular contraction and the ensuing ejection of blood from the ventricle, the pressure begins to decline and the aortic valve closes, creating a distinctive characteristic in the pressure waveform known as the dicrotic notch. The last phase of the cardiac cycle is known as diastole. During diastole, there is an exponential decay in pressure to a minimum value (the diastolic pressure). This is then followed by the next contraction of the left ventricle, creating the onset of the next cardiac cycle.

The exact shape of the blood pressure waveform created within an individual is a function of individual anatomical physiological parameters. Factors such as the strength of the ventricular contractions, heart rate, compliance of the arterial walls, degree of cardiovascular disease and many other factors all interact to create the specific morphology of an individual's blood pressure waveform. Furthermore, this morphology can change from moment to moment as factors such as strength of contractions, degree of activity, type of drug therapy, and many other possible parameters change.

Figure 2:
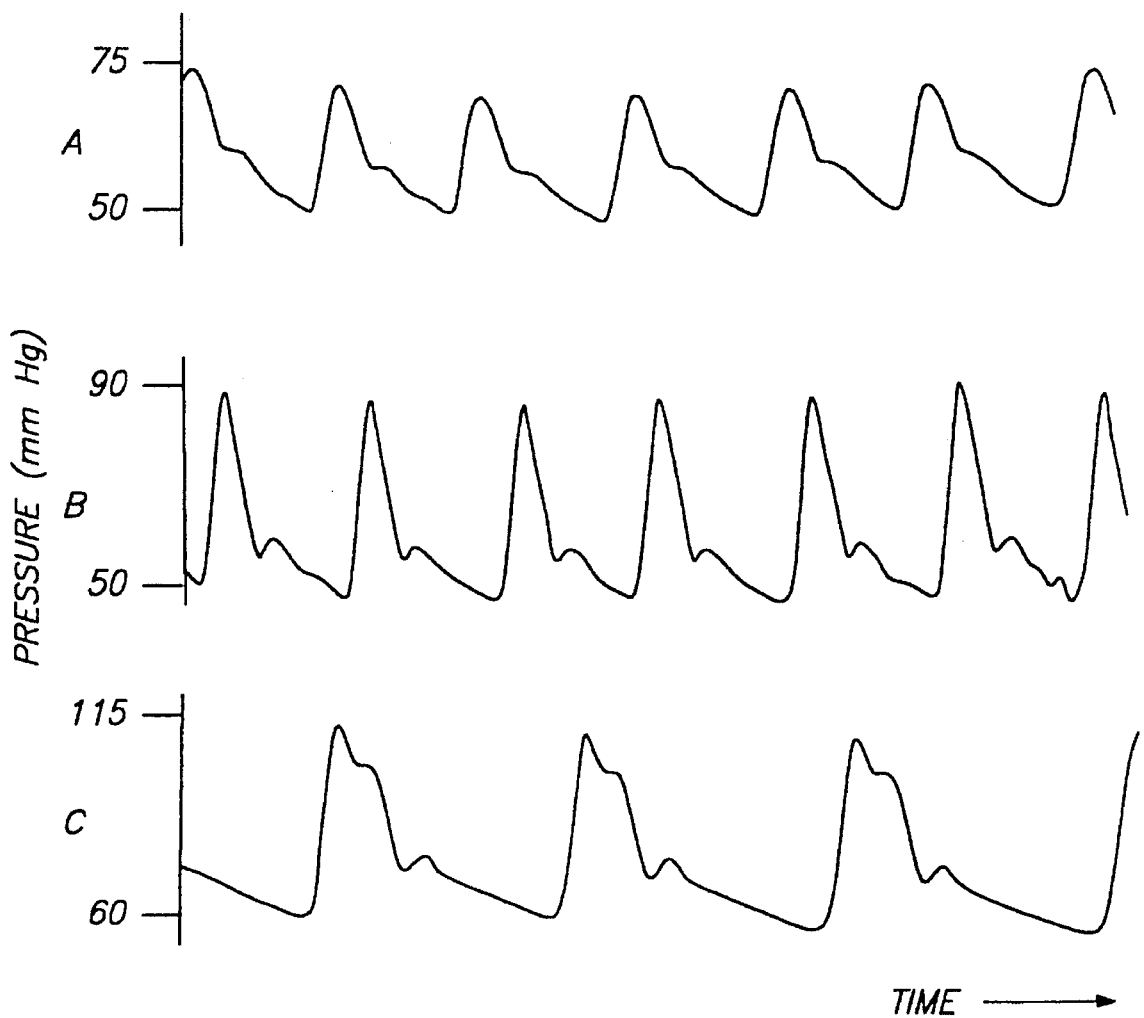
FIG. 2 shows actual intra-arterial blood pressure waveforms recorded on a first patient undergoing surgery. These waveforms depict the changes in morphology that accompany blood pressure changes.
Figure 3:
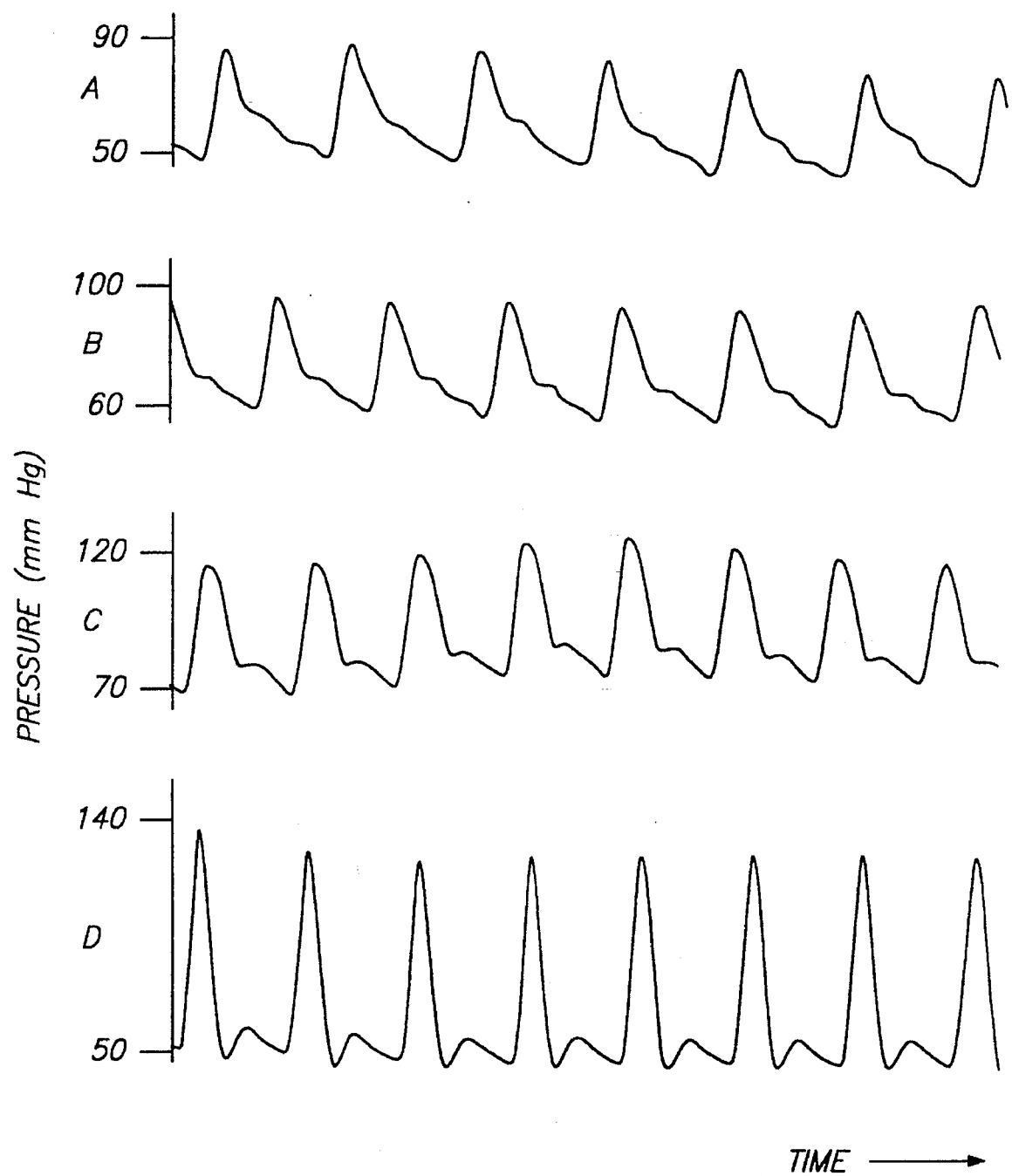
FIG. 3 shows actual intra-arterial blood pressure waveforms recorded on a second patient undergoing surgery. These waveforms depict the changes in morphology that accompany blood pressure changes.
Figure 4:
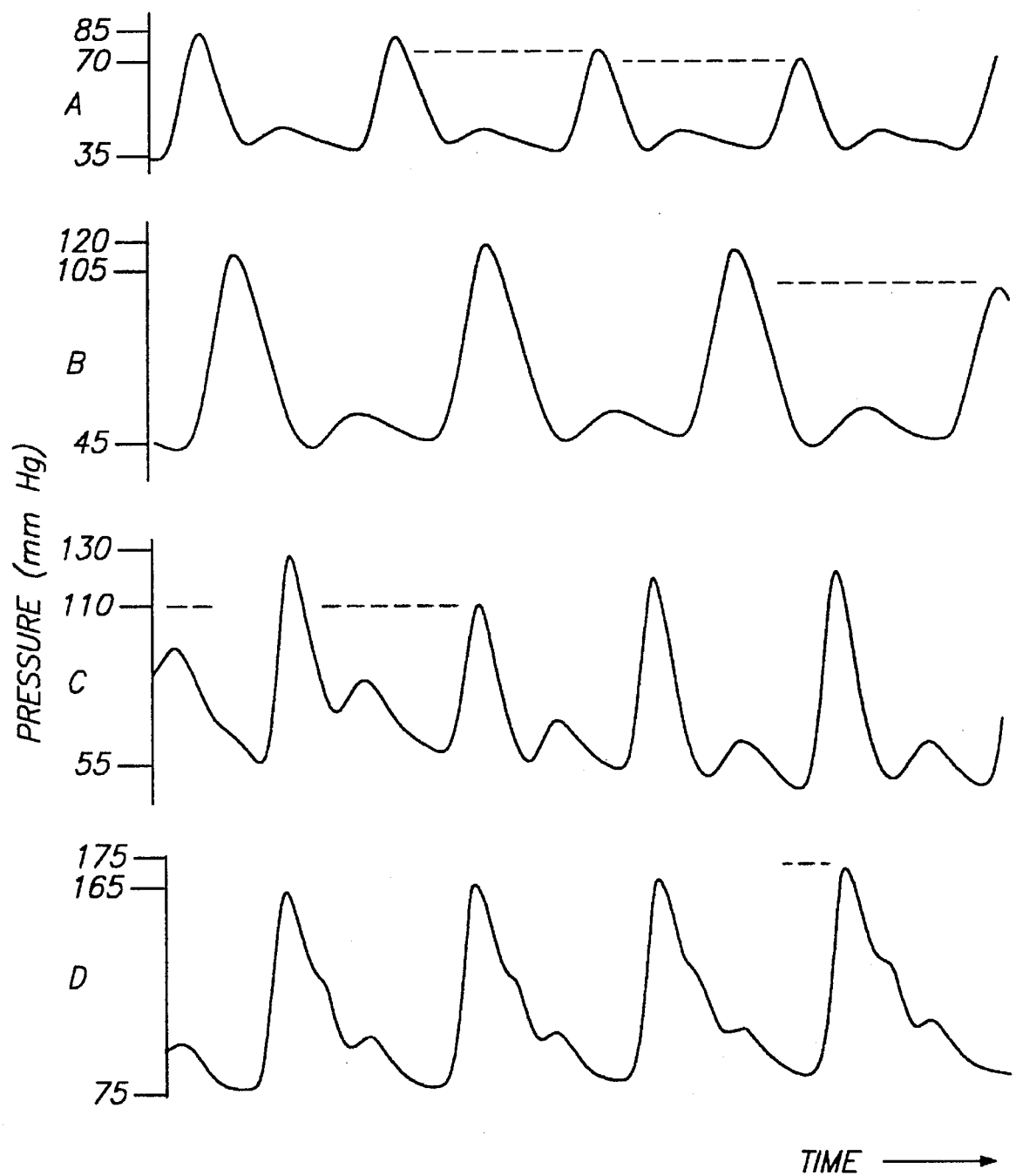
FIG. 4 shows actual intra-arterial blood pressure waveforms recorded on a third patient undergoing surgery. These waveforms depict the changes in morphology that accompany blood pressure changes.

FIGS. 2, 3 and 4 show actual blood pressure waveforms of three different patients obtained with intra-arterial catheters that were recorded during surgery. For each of these patients, waveforms are shown as the blood pressure varies from low values to higher values. The pressure of the patient in FIG. 2 changes from a systolic/diastolic value of 75/50, through 90/50 and then to 115/60. These pressure changes are accompanied by changes in waveform morphology, and can be very dramatic over short periods of time. This phenomenon is also depicted in FIGS. 3 and 4, where the systolic pressure rises to even higher values. In addition, substantial changes from one beat to the next are shown in FIG. 4.

FIG. 5 shows two waveforms that appear to be nearly identical. The upper waveform was obtained using a piezoelectric sensor, and the lower one with an intra-arterial catheter. While changes in the beat-to-beat pressure are observable, an improved picture of these changes is shown in FIG. 6. The representation shown here was created by performing a short time Fourier analysis to obtain the frequency components of the first four beats shown in FIG. 5A, and then combining them with the time varying components. The graph shows that the signal power contained in each of these beats is substantially different.

The present invention includes a procedure that reverses the process depicted in FIGS. 2–6. The collective action of the various components of an individual's cardiovascular system combine to form the specific blood pressure waveform that is detected by the invasive and noninvasive sensors. The preferred method of the present invention breaks the waveform into its constituent components, and then analyzes the instantaneous changes in these components to determine changes in the physiological parameters of interest. These constituent components are referred to as "features" in this specification. Because of the multivariate influence of parameters such as myocardial contractility, vasomotor tone, peripheral vascular resistance, wave velocity, incidence of reflected waves, heart rate and other factors, sophisticated methods such as modern pattern recognition techniques are useful in determining the relationship between waveshape change and blood pressure change.

In addition, this technique is used to analyze and track other physiological variables such as vascular wall compliance, changes in the strength of ventricular contractions, changes in peripheral vascular resistance, changes in fluid volume, changes in cardiac output, myocardial contractility and other related factors.

BLOOD PRESSURE MONITOR SYSTEM

Figure 7:
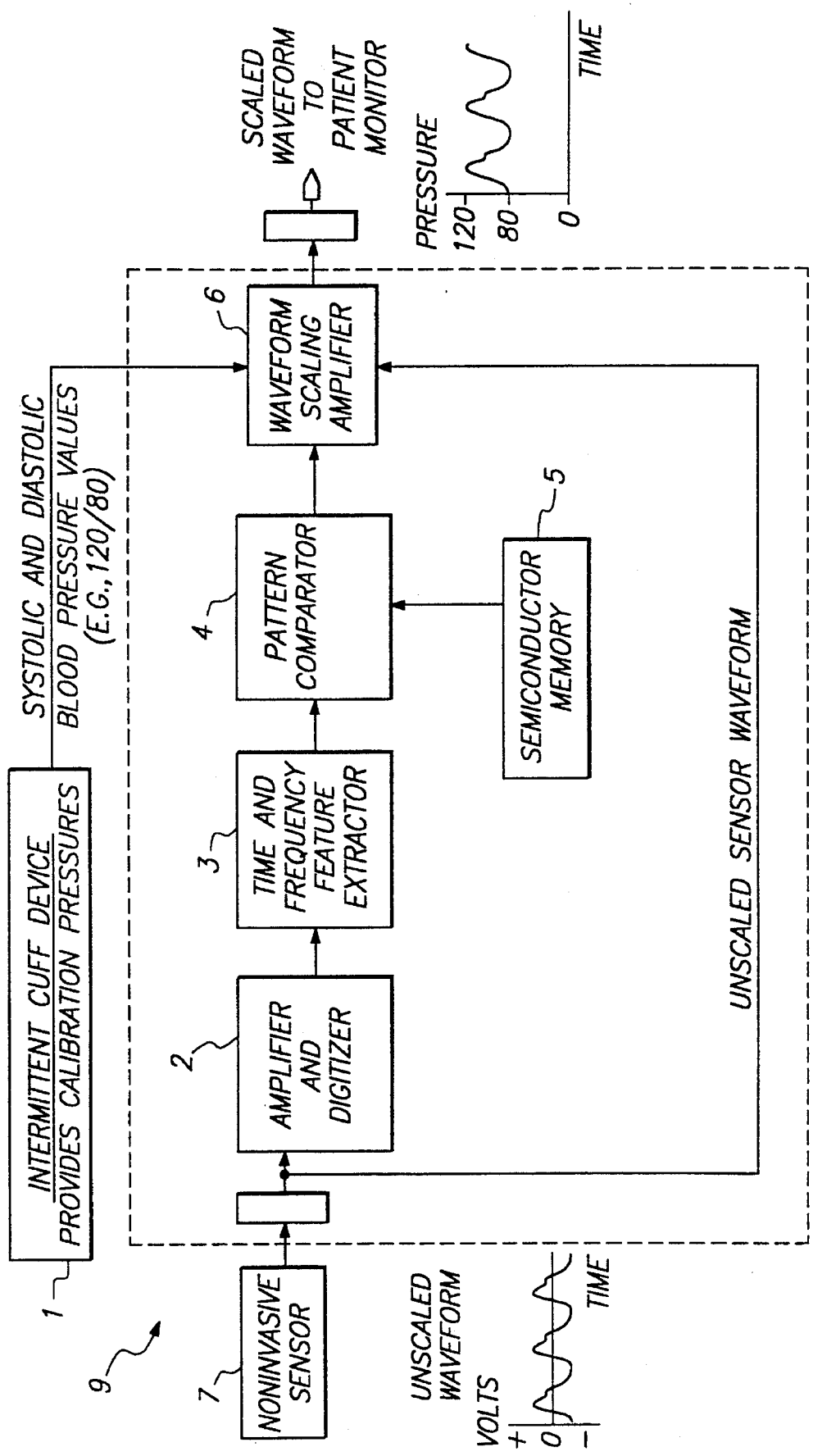
FIG. 7 is a block diagram showing the main components comprising the preferred embodiment of the blood pressure monitor.

FIG. 7 is a block diagram showing the main components of the preferred embodiment of the blood pressure monitor. There is an intermittent cuff device 1, a noninvasive sensor 7 and a processor 9. The processor further comprises amplifier and digitizer 2, time and frequency feature extractor 3, pattern comparator 4, memory 5, and waveform scaling amplifier 6.

In operation, following proper application of the noninvasive sensor 7 over the patient's artery, the user manually initiates the first calibration reading. Intermittent cuff device 1 inflates and then slowly deflates an occlusive cuff while monitoring the signals created by blood flow through the artery underlying the cuff. The pressure values obtained represent the patient's true blood pressure and are the first calibration values, i.e., the first systolic and diastolic blood pressure values. These calibration values are stored in the waveform scaling amplifier 6.

Alternatively, noninvasive sensor signals taken during a calibration blood pressure reading can serve to identify the diastolic and systolic pressures representing the patient's absolute blood pressure. In this manner, the noninvasive sensor can serve to communicate the calibration blood pressure values to the scaling amplifier for storage.

Immediately following cuff deflation, amplifier and digitizer 2 begins sampling the noninvasive sensor 7 signals representing the patients physiological functions. Feature extractor 3 processes and analyzes several consecutive pulses to provide a representative set of features to pattern comparator 4. These initial noninvasive sensor signal features are stored in the pattern comparator and serve as the reference point from which the ongoing continuous changes are determined.

Alternatively, noninvasive sensor signal features from pulses occurring before a calibration blood pressure reading can be stored in the pattern comparator and these historical features can serve as the reference point from which ongoing continuous changes are determined. Another alternative is a combination of noninvasive sensor signal features from pulses occurring before a calibration blood pressure reading and noninvasive sensor signal pulses occurring after a calibration blood pressure reading can be stored in the pattern comparator and this combination of historical features can serve as the reference point from which ongoing continuous changes are determined. Finally, noninvasive sensor signal features from pulses occurring during a calibration blood pressure reading can be stored in the pattern comparator and these features can serve as the reference point from which ongoing continuous changes are determined.

As the patient is monitored, the amplifier and digitizer 2 continuously sample the noninvasive sensor signals. Each successive sensor pulse is sampled, and the samples are sent to time and frequency feature extractor 3. The features are extracted and sent to the pattern comparator 4. The pattern comparator compares the current features against initial sensor signal features and predetermined features. Predetermined features are stored in memory 5 and provide a relationship of incremental blood pressure change information as a function of feature inputs. The development of the predetermined features is discussed in detail under a separate heading. Pattern comparator 4 then provides these incremental change values to scaling amplifier 6, which appropriately adjusts the sensor waveform applied directly to the waveform scaling amplifier 6.

As described above, normally, the amplifier and digitizer continuously sample the noninvasive sensor signals. However, in some situations, it may be preferable to periodically or intermittently sample the noninvasive sensor. The preferred embodiment of the present invention is capable of performing intermittent or periodic sampling of the noninvasive sensor by changing the sampling function of the amplifier and digitizer 2.

The blood pressure waveform can change quickly and, therefore, the apparatus must be equipped to handle the data. In the preferred embodiment, the sampling period is 2 milliseconds resulting in 500 samples per second with 8 bits per sample. Because these samples are processed in real time on a pulse-by-pulse basis, a high performance digital signal processor is chosen. A DSP chip such as a TMS-320C20 made by Texas Instruments is used in the preferred embodiment and has been found to satisfactorily perform the method of the present invention.

From a clinical standpoint, it is desirable to have the updated waveform information as rapidly as possible, but without drastic beat-to-beat changes. For this reason, waveform scaling amplifier 6 may also average the waveform over several beats, such as four to eight beats, to provide smoother information to the output.

Figure 9:
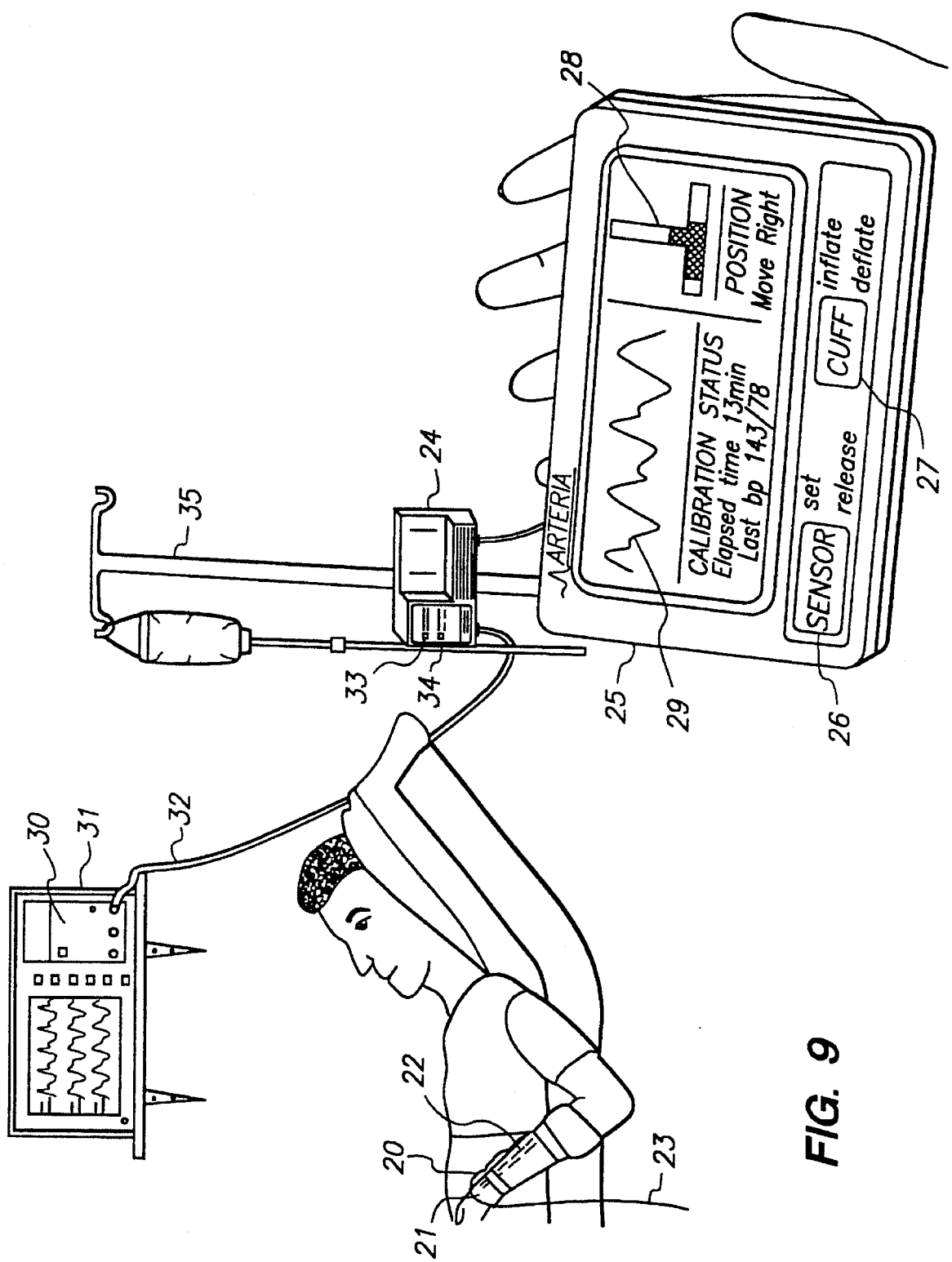
FIG. 9 is a pictorial representation of the functional hardware implementation of the preferred embodiment.

The output from scaling amplifier 6 is presented to the intraarterial blood pressure input channel of a conventional patient monitor 31 (as shown in FIG. 9). Alternatively, the device herein disclosed may have a self-contained waveform interpretation and display capability. The blood pressure information may be displayed as a waveform with numerical values, waveform alone, or numerical values alone.

In the preferred embodiment, intermittent cuff device 1 is used to obtain periodic calibration pressure values. These values may alternatively be manually obtained with a cuff and stethoscope or an automated intermittent cuff device, and input as calibration values, or may be obtained from an intra-arterial catheter. Periodic recalibration times may be from 2 to 60 minutes or longer.

The periodic recalibration can also occur automatically when the processor 9 detects a predetermined criteria. In this embodiment, the pattern comparator 4 compares current sensor signal features with a reference point of the initial features obtained during calibration. When a difference in these features meets predetermined criteria, the comparator indicates that a recalibration should be performed. An example of predetermined criteria is a ratio of change in mm of Hg per unit time. For example, a blood pressure change of 20 mm Hg in 30 seconds may satisfy the criteria while a change of 20 mm Hg over 1 hour may not satisfy the criteria.

Figure 8:
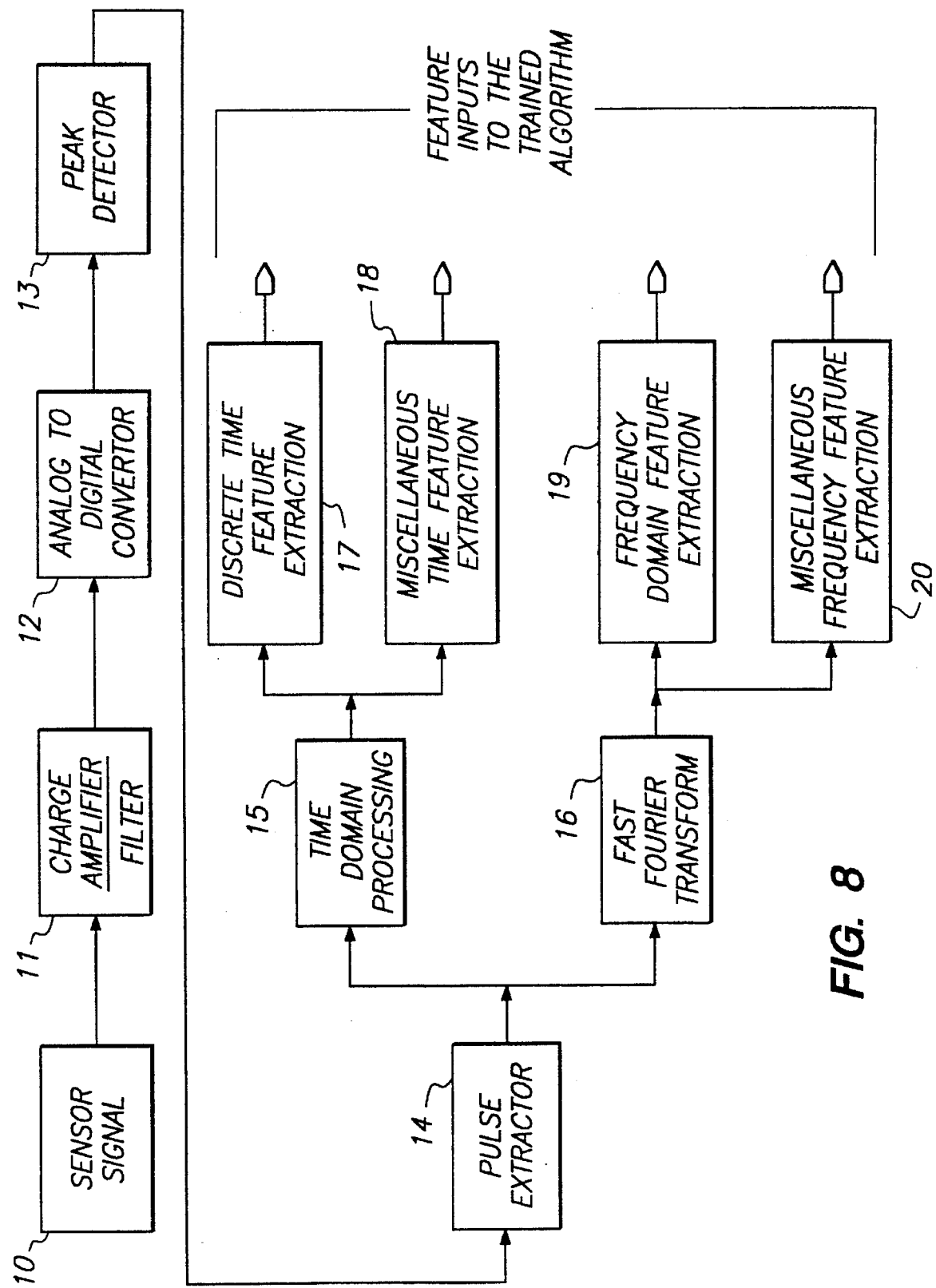
FIG. 8 is a block diagram showing the signal processing elements used to extract the features fed to the trained algorithm resulting in blood pressure change values.

FIG. 8 is a block diagram of the main components comprising the signal processing portion of the blood pressure measurement device. Sensor signal 10 is amplified and filtered by charge amplifier/filter 11. Digitizer 12 converts the waveform from analog to digital form, and passes the data to peak detector 13.

Peak detector 13 identifies each pulse waveform corresponding to one cardiac cycle by identifying the point on the pressure waveform corresponding to the peak (systolic) pressure, which is taken as the point of maximum amplitude. It should be noted that while this point on the waveform does correspond to the peak pressure point, it is a relative measure, and not an absolute pressure value. This value may move in direct or inverse proportion to the actual pressure, but will still coincide with the peak pressure.

Following identification of the peak, pulse extractor 14 identifies the end point of the last pulse and the beginning point of the next pulse as essentially the beginning and end of the current pulse. The extracted pulse is then fed in parallel to two processing elements—time domain processor 15 and Fast Fourier Transform (FFT) processor 16.

A. TIME DOMAIN PROCESSING

Time domain processor 15 provides two sets of features known as discrete time features and miscellaneous time features. The discrete time features comprise the individual samples of the waveform. The quality of these features has been previously determined, one at a time, by an iterative process beginning with the single best feature. The single best feature is defined as the one which, by itself, gives the highest accuracy for all of the blood pressure pulses presented as input data, when compared to the absolute blood pressure value obtained during the historical data acquisition process (described below). The iterative process is repeated, except this time searching for the second best feature, which in conjunction with the best feature gives the greatest accuracy. The iterative process then continues with the third, fourth and up to the Nth best features.

The quality of the first set of features, known as discrete time features, are determined by applying one of three forms of analysis to the historical data acquisition. The first form is curve fit comparison, the second form is classification comparison, and the third form is comparison to features selected during training by a neural network.

The quality of the second set of features, known as miscellaneous time features, are determined by applying more traditional analysis to the waveform. Among these features are pulse amplitude, rise time, decay time, pulse width, skew, kurtosis, repetition rate from one pulse to the next, the pulse RMS value, and other parameters. These features are determined for each pulse and are then presented to feature extraction algorithm 18.

In the preferred embodiment, the sampling period is 2 milliseconds resulting in 500 samples per second with 12 bits per sample. This sampling rate and bits per sample have been found to produce features sufficient for use in the present invention. A variation in sampling rate or bits per sample should also produce features sufficient for use in the present invention.

B. FREQUENCY DOMAIN PROCESSING

In parallel with the time domain processing, each digitized, individual pulse is transformed to the frequency domain by Fast Fourier Transform (FFT) 16. The same iterative procedures discussed above under time domain processing are followed in the frequency domain processing to extract frequency features and miscellaneous frequency features. Among these features are the individual FFT sample values, maximum power frequency, frequency shifts over time, phase relationships among samples, overall frequency curve shape, and other parameters.

For example, frequency domain feature extractor 19 selects each frequency feature, one at a time, within a range of 0 to 40 Hz, in ¼ Hz increments, and through the same iterative selection process described above, determines the single best frequency feature.

In the preferred embodiment, the sampling period is 2 milliseconds resulting in 500 samples per second with 12 bits per sample. The Fourier transform size is 1024 points (1K), which is performed by a Fast Fourier Transform (FFT) procedure, but could also be performed by a Discrete Fourier Transform (DFT) procedure or other frequency domain transform. The sampling rate, transform size and bits per sample have been found to produce features sufficient for use in the present invention. A variation in sampling rate, transform size or bits per sample should also produce features sufficient for use in the present invention.

C. FEATURE PROCESSING

Feature processing is the procedure of comparing features of the present patient's blood pressure waveform data against that of historical patient's blood pressure waveform data. In FIG. 7, the noninvasive signal is processed by feature extractor 3, then the pattern comparator 4 compares the noninvasive signal features against predetermined features stored in memory 5. The accumulation of historical data is important to the present invention because it permits the evaluation of current data against prior known data to most accurately determine the patient's blood pressure.

The historical data acquisition process comprises gathering two sets of blood pressure data from a plurality of patients in a variety of clinical situations. The first set of data is the actual blood pressure obtained, for example, using conventional intra-arterial catheters and associated pressure transducers. The second set of data is obtained from a noninvasive sensor, typically placed over the radial artery in the opposite arm. This acquired data may serve as predetermined data in the pattern comparison of FIG. 7, or the data may be used to train a neural network algorithm as in the preferred embodiment. Historical data acquisition is discussed in detail below under a separate heading.

The features from the predetermined data and the present patient data must be processed to provide meaningful results indicating the patient's blood pressure. Important features for evaluation include time features such as individual samples, pulse amplitude, rise time, decay time, pulse width, skew, kurtosis, repetition rate from one pulse to the next, pulse RMS value, and other parameters. Other important features for evaluation include frequency features such as individual FFT samples, maximum power frequency, frequency shifts over time, phase relationships among samples, overall frequency curve shape, and other parameters.

The processor 9 executes a procedure to compare the sampled noninvasive sensor signal features with predetermined features. A first form of this procedure is essentially a curve fitting procedure that compares the sample points against known curves and produces an output signal indicative of whether the fit compared to each of the curves is good or poor. A second form of this procedure is a classification procedure that compares the sample points against a variety of classification criteria and outputs a signal indicative of whether a specific classification is good or poor. The processor can interpolate among the classifications to determine relevant features of the sampled sensor signal. A third form of this procedure is the preferred form that compares the sample points against a variety of feature criteria selected during training on historical data by a neural network. This third form uses an algorithm to assist in comparing the sample points in order to determine the patient's blood pressure. A discussion of how the algorithm is developed is discussed below under a specific heading.

Because there are potentially many thousands of time, frequency and miscellaneous features, plus various combinations of each of these types of features, the feature selection process can be very time consuming, even with today's high performance computers and workstations. For this reason, it is helpful to put an upper limit on the number of features used. This limit may be chosen as a fixed number of features or may be chosen as the number of features at which the improvement in accuracy is not significant enough to justify the time required. It may also occur that the addition of features beyond a certain number can cause a decrease in accuracy. In the preferred embodiment, it was determined that the best performance for the set of patient data used in the training process was obtained using a combination of frequency domain and miscellaneous time features, and that maximum accuracy occurred typically with 10 to 15 features. A greater number of features can be used to further develop the present invention. For example, embodiments using 100 features, 200 features or more have been considered as a means of obtaining greater accuracy.

FIG. 9 shows pictorially a preferred embodiment of the blood pressure measurement system. Sensor 20 is attached to the subject's wrist 21 over radial artery 22. Sensor lead 23 is connected to amplifier/control housing 24. Housing 24 contains the signal processing amplifiers, electronic circuitry for digitizing the sensor signals, conventional computer components such as RAM for data storage, PROM for program memory, a CPU, digital signal processing circuitry, associated I/O circuitry, and a power supply. Also contained in housing 24 is means for activating and controlling a conventional blood pressure cuff, including a small air pump, pressure transducer, a microcomputer for controlling these devices and for determining the subject's blood pressure on an intermittent basis.

Removable control and display panel 25 contains means 26 for activating a sensor hold down device, means 27 for activating the cuff to obtain an initial calibration pressure or in the event periodic calibration check pressures are desired, means 28 for indicating the position of sensor 20 with respect to artery 22, and means 29 for displaying the waveform obtained from the sensor. Other useful information such as the last calibration pressures, elapsed time since the last calibration reading, and other useful clinical information may also be displayed.

Finally, housing 24 contains output circuitry that allows the calibrated blood pressure waveform, which has been detected by sensor 20, amplified, processed and scaled, to be output to invasive blood pressure input channel 30 on most commercially available patient monitors 31, via cable 32. This provides a noninvasive, continuous signal for display. In another embodiment, the control and display panel 25 displays the calibrated blood pressure waveform.

Housing 24, which also contains means 33 for applying and removing power to the electronic circuitry, and means 34 for sending a zero pressure calibration pulse to patient monitor 31, is small and lightweight, and can therefore be easily mounted on IV pole 35, at the patient's bed, or other suitable location.

HISTORICAL DATA ACQUISITION

The historical data acquisition process comprises gathering two sets of blood pressure data from a plurality of patients in a variety of clinical situations. This is necessary so that enough data is provided to the training algorithm to permit patterns relating waveform features to blood pressure changes to develop. A minimum of twenty-five to thirty patients is recommended, although three to four times that number is preferable.

The first set of data is the actual blood pressure obtained, for example, using conventional intra-arterial catheters and associated pressure transducers. These catheters are routinely inserted during many types of surgeries, usually in the patient's radial artery. If sufficient data cannot be collected using intra-arterial catheters, intermittent occlusive cuff devices may be used, provided the values obtained can be correlated with the appropriate waveshape. The signal obtained from the pressure transducer is digitized and stored in a data acquisition system. This becomes the reference data, i.e., the data that serves as the absolute, true value of the individual's blood pressure.

Figure 10:
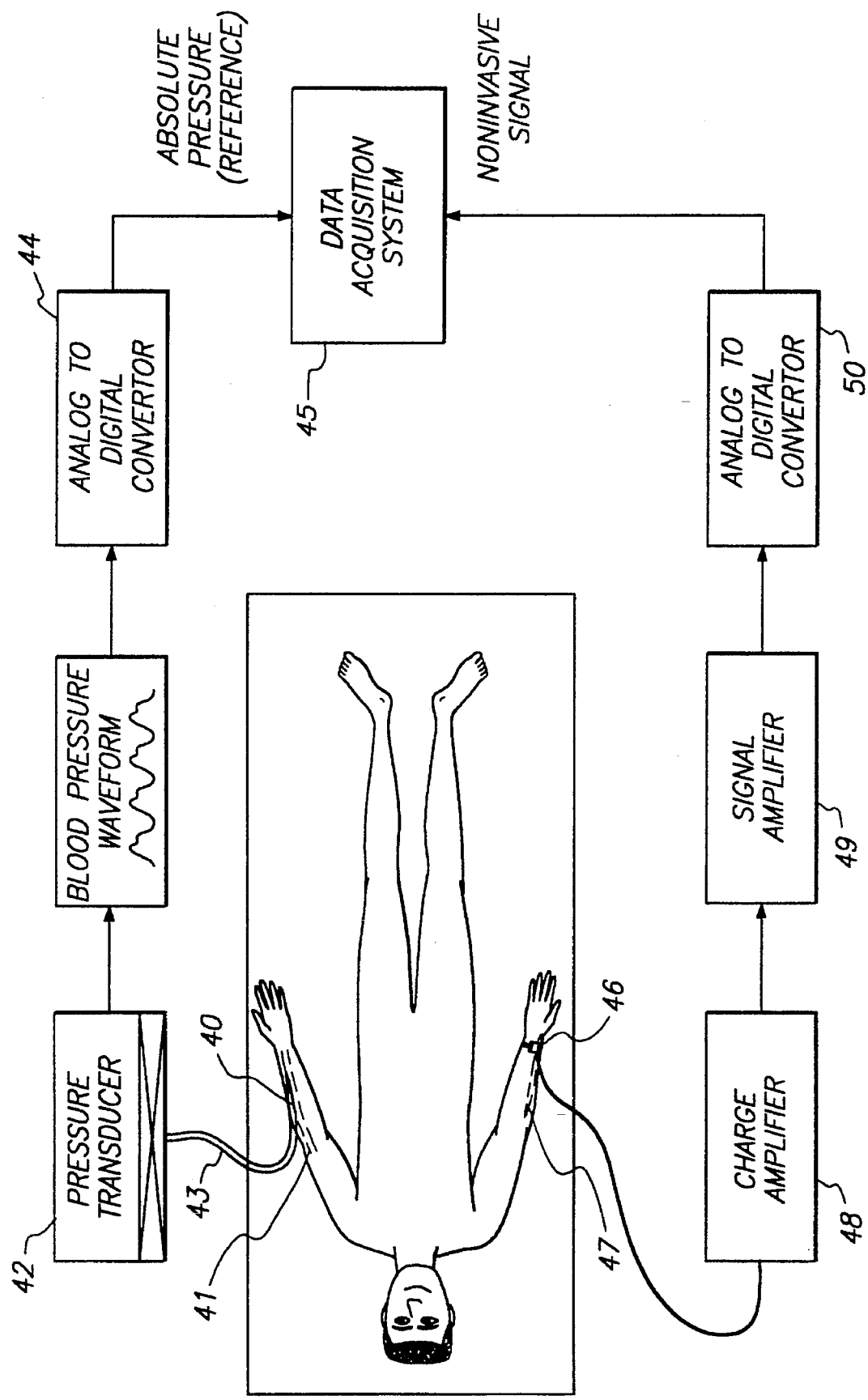
FIG. 10 is a diagram showing the main elements used to acquire and store the data used in training the algorithm.

FIG. 10 shows an intra-arterial catheter 40 inserted into blood vessel 41 (radial artery) in the arm of an individual. Catheter 40 is attached to pressure transducer 42 via fluid filled line 43. As blood is forced through artery 41 by the pumping action of the heart, the pulsatile pressure wave is transmitted to pressure transducer 42 through line 43. The transducer converts the pressure wave into an electrical analog. Digitizer 44 converts the analog signal to digital form using a sampling technique. The digitized signal is stored in data acquisition system 45.

The second set of data is obtained from a noninvasive sensor, typically placed over the radial artery in the opposite arm. The waveform detected by this sensor is created by the pressure wave within the artery, but is generally modified during transmission to the surface by the arterial wall and by the overlying tissue. The signal from this sensor is also digitized, and is simultaneously stored in the data acquisition system.

Noninvasive sensor 46 is positioned over artery 47 in the opposite arm of the same individual. The pressure wave within the artery is transmitted to sensor 46 through arterial wall and overlying tissue. Sensor 46 may employ one or more of several technologies for detecting the waveform. A sensor constructed of piezoelectric film was chosen for this embodiment.

Advantages of a piezo film sensor include simplicity of construction, high sensitivity to weak signals and adaptability to a variety of anatomical sites. Because many clinical situations require that the sensor be disposable, cost is also important. Piezo film sensors readily lend themselves to cost-effective manufacture.

A disadvantage of piezoelectric film is its sensitivity to motion artifact. This problem was minimized by the development of a three-element sensor as outlined in O'Sullivan, et al., U.S. patent application Ser. No. 08/059,425. In this sensor, two outside elements, positioned on either side of the artery being monitored, detect primarily artifact, whereas the center element, centered over the artery, detects both the pressure wave and artifact. The signals from the two outside elements are summed and then subtracted from the center element, thereby canceling the artifact.

The signal from sensor 46 is input to charge amplifier 48 and amplified by signal amplifier 49. Digitizer 50 converts the analog signal to digital form using a sampling technique. The digitized signal is stored in data acquisition system 45 in time synchronization with the intra-arterial signal.

The data acquisition system for gathering historical data comprises an analog to digital (A/D) converter for digitizing the above mentioned input signals. In the preferred embodiment the sample period is 2 milliseconds resulting in 500 samples per second and there are 12 bits per sample. The data acquisition system records the digitized data, for example, on a hard disk drive, and may also contain a tape drive. This acquired data may serve as predetermined data in the pattern comparison of FIG. 7, or the data may be used to train a neural network algorithm as in the preferred embodiment. An example of training a neural network algorithm is described below.

DEVELOPING PREDETERMINED FEATURES

After data is gathered from a patient population, the data is analyzed to develop predetermined features. These predetermined features stored in memory 5 provide the pattern comparison unit 4 with meaningful data against which to compare the sensor signal features from feature extractor 3. This predetermined feature development can take several forms.

The first form is to develop data corresponding to predetermined curves. This is done by comparing curve fits of the historical data acquisition to develop relevant predetermined features. The second form is to develop data belonging to predetermined classes. This is done by comparing curves of the historical data acquisition to develop a variety of classes of curves having relevant predetermined features. The third form is to develop features selected during training by a neural network. The third form is the preferred form and is discussed in detail below.

The two sets of data gathered in the historical data acquisition process are then fed to the training algorithm. The training process is an off-line process, and is begun after sufficient data has been collected from a sampling of the patient population. Various types of training methods have been developed, and are generally known as pattern recognition techniques. For example, a classifier may be used to "classify" data in one of several categories, e.g., A or B, depending on the characteristics of the data. It follows that multiple categories may be set up to provide a more detailed classification of data. A newer technique is known as an artificial neural network (ANN), and is the technique of choice for this embodiment.

Figure 11:
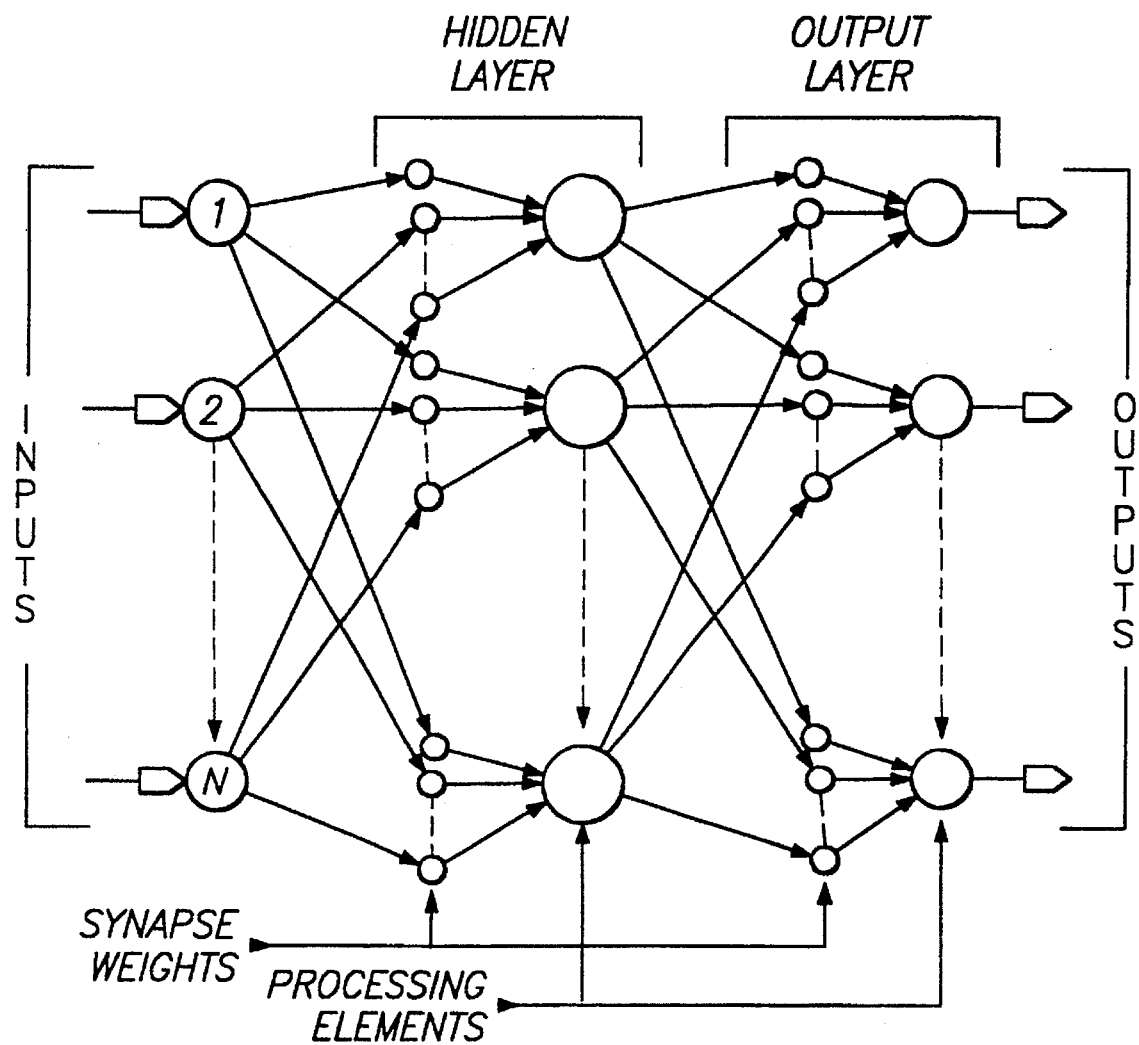
FIG. 11 is a diagram showing the basic elements of an Artificial Neural Network.

FIG. 11 is a basic diagram of a simple neural network. In its simplest form, a neural net comprises inputs, processing elements called neurons, synapse weights and outputs. An input and its weight are called a connection. The synaptic weights are the network's primary means of making inputs map accurately to outputs. The magnitude of each weight is determined by the value of each input. The learning process is a trial-and-error way of finding the correct weights.

Two key architectural features of practical neural networks are that every input is connected to every output, and that there are multiple layers. The output of one layer becomes an input to the next. Learning is accomplished by the designer choosing one of many available training algorithms.

There are a variety of commercially available neural networks, and they come in both hardware and software versions. The most commonly used version of learning algorithms is called Error Back Propagation. A version of this algorithm developed by the Hecht-Nielsen Company is used in the preferred embodiment.

The training process proceeds as follows: Both sets of data (Reference and sensor data) are filtered to remove unwanted artifact signal. The next step is to convert the data into a form that permits the extraction of features, a feature being defined as a distinguishing characteristic of a given waveform. The detected signal is a waveform whose amplitude varies with time. Various time domain features such as rise time, decay time, repetition rate, skew, kurtosis and other defining characteristics may be used to describe the time varying details of a given waveform.

In addition, an analysis of the frequency characteristics of a waveform provides significant additional information regarding the characteristics, or features of a waveform. By transforming the data from the time domain into the frequency domain, information about each of the individual frequencies that make up the waveform, and the relative magnitude and phase relationship of each of these frequencies, is obtained.

Various methods of transforming data from the time domain to the frequency domain exist in the current art, such as Fourier transforms, Laplace transforms, and others. The device described herein can utilize any of these methods.

Furthermore, as the blood pressure waveform changes in response to changes in the individual's blood pressure, or due to other factors, concurrent changes occur in the time/frequency characteristics of the waveform.

The invention here described provides a means for training an algorithm to predict the magnitude and direction of a blood pressure change by "recognizing" changes in the time/frequency characteristics of each successive waveform created by the pulsatile blood flow of an individual. The time/frequency analysis referred to above results in the identification of a set of features. The training process can be described mathematically as a transform T, such that $T(f_1, f_2 \ldots f_n)$ provides an estimate of blood pressure change, where $f_1, f_2 \ldots f_n$ are the selected set of features, and T is the transform obtained in the training process.

During the training process, all of the time/frequency features are presented as inputs to the neural network, e.g., on a pulse by pulse basis. At the same time, the absolute value of the Systolic, Diastolic and Mean Arterial Pressure, corresponding to each of these pulses is extracted from the intra-arterial pressure waveform and input to the network as the fiducial values. The network algorithm, through an exhaustive, iterative process, develops the set of features derived from the noninvasive sensor signal that provide the most accurate mapping, or transform, to the desired output blood pressure value.

For purposes of clarification, an example will be given. Assume that one pulse waveform has been selected from the sensor signal, and the corresponding blood pressure values have been extracted from the blood pressure transducer signal. Time domain features such as rise time, etc., have been determined, and all of the frequencies that make up this pulse (including magnitude and phase and/or real and imaginary parts) have been presented as inputs to the neural net. The network identifies the features that correlate with the blood pressure values for this sensor pulse. This process is repeated for all of the pulses in the training set. Since the shape of the waveform changes as the blood pressure changes, the features corresponding to these blood pressure values change. Furthermore, one individual may have the same systolic or diastolic blood pressure value as another, but might have a very different set of features if the shape of the waveform is different. Therefore, the network must select the set of features, from all of those presented to it, that best correlate to a given blood pressure. Since there will be different combinations of features that correlate to a given blood pressure, there will be multiple paths through the neural net leading to a given output.

Once the training process is completed, the predetermined features obtained reside in an EPROM or other memory device within the blood pressure monitor.

An alternative is to incorporate the ANN within the blood pressure monitor processor 9 to continuously refine the feature processing and to promote improved feature processing and feature recognition of the blood pressure monitor. This embodiment does not require predetermined features per se because the ANN can function to develop relevant features in real time or pseudo real time.

ALTERNATE EMBODIMENTS

A first alternate embodiment to the present invention is an ambulatory or other mobile blood pressure monitor. This embodiment has the same features as the preferred embodiment and is compact enough for an individual to carry outside a doctor's office or hospital. Mobility is beneficial because it permits the continuous sampling and storage of blood pressure data for periods of time when the individual is not directly supervised.

This ambulatory unit can also be dispatched with a paramedic to an emergency location. This mobile dispatch capability provides medical personnel with a constant monitor of the patient's blood pressure to determine proper medication and treatment. It also assists the medical personnel in tracking the blood pressure of the person as the emergency is resolved.

A second alternate embodiment is used in conjunction with an electrocardiogram (EKG). The blood pressure monitor records the patient's blood pressure waveform and correlates these results with those of the EKG. This correlation assists medical personnel in understanding the patient's condition.

Modifications and variations may be made to the disclosed embodiments without departing from the subject and spirit of the invention as defined by the following claims.

What is claimed is:

1. A blood pressure monitor for measuring a patient's blood pressure, comprising:
    memory means for storing reference features representative of blood pressure from a population of reference patients;
    means for periodically obtaining calibration blood pressure values from the patient, said calibration blood pressure values representing the patient's absolute blood pressure;
    means for noninvasively obtaining blood pressure pulses from the patient;
    processing means for processing said blood pressure pulses to obtain processed features representative of said blood pressure pulses;
    comparing means for comparing said processed features with said reference features to provide comparison signals representative of the comparison of said processed features with said reference features; and
    scaling means responsive to said calibration blood pressure values and said blood pressure pulses for scaling said comparison signals to provide the patient's true blood pressure.

2. The blood pressure monitor of claim 1, wherein:
    said means for noninvasively obtaining blood pressure pulses is a piezoelectric sensor.

3. The blood pressure monitor of claim 1, wherein:
    said processing means includes means for processing said blood pressure pulses to obtain processed time domain features representative of said blood pressure pulses.

4. The blood pressure monitor of claim 1, wherein:
    said processing means includes means for transforming said blood pressure pulses from the time domain to the frequency domain; and
    said processed features are frequency domain features.

5. The blood pressure monitor of claim 1, wherein:
    said processing means includes means for transforming said blood pressure pulses from the time domain to the frequency domain; and
    said processed features are a combination of time domain features and frequency domain features.

6. The blood pressure monitor of claim 1, wherein:
    said comparing means compares a curve fit of said processed features with said reference features.

7. The blood pressure monitor of claim 1, wherein:
    said comparing means compares a classification of said processed features with a classification of said reference features.

8. The blood pressure monitor of claim 1, wherein:
    said comparing means includes means for comparing said processed features with said reference features that are determined by a neural network.

9. The blood pressure monitor of claim 1, wherein:
    said memory means includes means for storing historical processed features as stored features, said stored features being one of the group consisting of historical processed features occurring before obtaining a calibration blood pressure value, historical processed features occurring after obtaining a calibration blood pressure value, historical processed features occurring before and after obtaining a calibration blood pressure value, and historical processed features occurring while obtaining a calibration blood pressure value; and
    said comparing means further includes means for comparing said processed features with said stored features to provide said comparison signals.

10. The blood pressure monitor of claim 1, wherein:
    said comparing means includes means for triggering said means for periodically obtaining calibration blood pressure values, when said comparing means detects a predetermined criteria.

11. The blood pressure monitor of claim 1, wherein:
    said comparing means includes a neural network.

12. A method of determining a patient's blood pressure comprising the steps of:
    storing reference features representative of blood pressure from a population of reference patients;
    periodically obtaining calibration blood pressure values from the patient, said calibration blood pressure values representing the patient's absolute blood pressure;
    noninvasively obtaining blood pressure pulses from the patient;
    processing said blood pressure pulses to obtain processed features representative of said blood pressure pulses;

comparing said processed features with said reference features to provide comparison signals representative of the comparison of said processed features with said reference features; and scaling said comparison signals with respect to said calibration blood pressure values and said blood pressure pulses to provide the patient's true blood pressure.

13. The method of claim 12, wherein:

said processing step includes obtaining time domain features.

14. The method of claim 12, wherein:

said processing step includes a step of transforming said blood pressure pulses from the time domain to the frequency domain; and said processing step includes obtaining frequency domain features.

15. The method of claim 12, wherein:

said processing step includes a step of transforming said blood pressure pulses from the time domain to the frequency domain; and said processing step includes obtaining a combination of time domain features and frequency domain features.

16. The method of claim 12, wherein:

said comparing step includes comparing a curve fit of the processed features with said reference features.

17. The method of claim 12, wherein:

said comparing step includes comparing a classification of the processed features with a classification of said reference features.

18. The method of claim 12, wherein:

said comparing step includes comparing the processed features with said reference features, wherein said reference features are determined by a neural network.

19. The method of claim 12, further comprising the step of:

storing historical processed features as stored features, said stored features being one of the group consisting of historical processed features occurring before obtaining a calibration blood pressure value, historical processed features occurring after obtaining a calibration blood pressure value, historical processed features occurring before and after obtaining a calibration blood pressure value, and historical processed features occurring while obtaining a calibration blood pressure value; and wherein said comparing step further includes comparing said processed features with said stored features to provide said comparison signals.

20. The method of claim 12, wherein:

said comparing step includes initiating said calibration step when said comparing step detects a predetermined criteria.

21. A monitor for measuring a waveform representing a patient's physiological function, said monitor comprising:

memory means for storing reference features representative of reference waveforms from a population of reference patients, said reference waveforms being representative of the reference patients' physiological function;

means for periodically obtaining a calibration waveform from the patient representative of the patient's physiological function;

means for obtaining a waveform representative of the patient's physiological function;

processing means for processing said obtained waveform to obtain processed features;

comparing means for comparing said processed features with said reference features to provide a comparison signal; and means responsive to said calibration waveform and said obtained waveform for scaling the comparison signal to provide a signal representative of the patient's physiological function.

22. A monitor as in claim 21, wherein:

said memory means includes means for storing reference features representative of reference waveforms from a population of reference patients, said reference waveforms being representative of the reference patients' blood flow;

said means for periodically obtaining a calibration waveform from the patient includes means for obtaining a calibration waveform representative of the patient's blood flow;

said means for obtaining a waveform representative of the patient's physiological function includes means for obtaining a waveform representative of the patient's blood flow; and said means responsive to said calibration waveform and said obtained waveform for scaling the comparison signal to provide a signal representative of the patient's physiological function includes means responsive to said calibration waveform and said obtained waveform for scaling the comparison signal to provide a signal representative of the patient's blood flow.

23. A monitor as in claim 21, wherein:

said memory means includes means for storing reference features representative of reference waveforms from a population of reference patients, said reference waveforms being representative of the reference patients' blood pressure;

said means for periodically obtaining a calibration waveform from the patient includes means for obtaining a calibration waveform representative of the patient's blood pressure;

said means for obtaining a waveform representative of the patient's physiological function includes means for obtaining a waveform representative of the patient's blood pressure; and said means responsive to said calibration waveform and said obtained waveform for scaling the comparison signal to provide a signal representative of the patient's physiological function includes means responsive to said calibration waveform and said obtained waveform for scaling the comparison signal to provide a signal representative of the patient's blood pressure.

24. A monitor as in claim 21, wherein:

said memory means includes means for storing reference features representative of reference waveforms from a population of reference patients, said reference waveforms being representative of the reference patients' physiological function, where said physiological function is one of the group consisting of blood pressure, heart beat, vascular wall compliance, strength of vascular contractions, vascular resistance, fluid volume, cardiac output, and myocardial contractility;

said means for periodically obtaining a calibration waveform from the patient includes means for obtaining a calibration waveform representative of the patient's physiological function, where said physiological function is one of the group consisting of blood pressure, heart beat, vascular wall compliance, strength of vascular contractions, vascular resistance, fluid volume, cardiac output, and mlyocardial contractility;

said means for obtaining a waveform representative of the patient's physiological function includes means for obtaining a waveform representative of the patient's physiological function, where said physiological function is one of the group consisting of blood pressure, heart beat, vascular wall compliance, strength of vascular contractions, vascular resistance, fluid volume, cardiac output, and myocardial contractility; and said means responsive to said calibration waveform and said obtained waveform for scaling the comparison signal to provide a signal representative of the patient's physiological function includes means responsive to said calibration waveform and said obtained waveform for scaling the comparison signal to provide a signal representative of the patient's physiological function, where said physiological function is one of the group consisting of blood pressure, heart beat, vascular wall compliance, strength of vascular contractions, vascular resistance, fluid volume, cardiac output, and myocardial contractility.

25. The monitor of claim 21, wherein:

said memory means for storing reference features representative of reference waveforms from a population of reference patients includes means for storing reference features that are determined by a neural network, said reference waveforms being representative of the reference patients' physiological function.

26. A method of monitoring a patient's physiological function, comprising the steps of:

storing reference features representative of reference waveforms from a population of reference patients, said reference waveforms being representative of the reference patients' physiological function;

periodically obtaining a calibration waveform from the patient, said calibration waveform being representative of the patient's physiological function;

obtaining a waveform representative of the patient's physiological function;

processing said obtained waveform to obtain processed features;

comparing said processed features with said reference features to provide a comparison signal; and scaling the comparison signal with respect to the calibration waveform and the obtained waveform to provide a signal representative of the patient's physiological function.

27. The method of claim 26, wherein:

said physiological function is related to the patient's blood flow.

28. The method of claim 26, wherein:

said physiological function is blood pressure.

29. The method of claim 26, wherein:

said physiological function is one of the group consisting of blood pressure, heart beat, vascular wall compliance, strength of vascular contractions, vascular resistance, fluid volume, cardiac output, and myocardial contractility.

30. The method of claim 26, wherein:

said storing step includes the step of storing reference features determined by a neural network and representative of reference waveforms from a population of reference patients said reference waveforms being representative of the reference patients' physiological function.

* * * * *